United States Patent [19]

Sato et al.

[11] 4,197,256

[45] Apr. 8, 1980

[54] METHOD OF STABILIZING AN ALKALINE AQUEOUS SOLUTION OF THIOUREA DIOXIDE

[75] Inventors: Kanji Sato; Kazuyoshi Kushibe; Masaru Nishii; Yasuhiro Kanaya; Yasumasa Kawabe, all of Fuji, Japan

[73] Assignee: Tokai Denka Kogyo Kabushiki Kaisha, Tokyo, Japan

[21] Appl. No.: 12,310

[22] Filed: Feb. 15, 1979

[30] Foreign Application Priority Data

Aug. 24, 1978 [JP] Japan .......................... 53/102357[U]

[51] Int. Cl.$^2$ ........................................... C07C 145/00
[52] U.S. Cl. ................................................ 260/513.7
[58] Field of Search ...................................... 260/513.7

[56] References Cited

U.S. PATENT DOCUMENTS

| 2,150,921 | 3/1939 | Havas | 260/513.7 |
| 2,493,471 | 1/1950 | Tillitson | 260/513.7 |

OTHER PUBLICATIONS

Nakagawa et al., Tetrahedron Letters, 1972, pp. 343–346.

Primary Examiner—Nicky Chan
Attorney, Agent, or Firm—Scully, Scott, Murphy & Presser

[57] ABSTRACT

According to this invention, there is provided a method of stabilizing an alkaline aqueous solution of thiourea dioxide characterized in that one or more substances selected from the group consisting of aliphatic ketones, alicyclic ketones and aliphatic dialdehydes are added to the said alkaline aqueous solution of thiourea dioxide.

5 Claims, No Drawings

METHOD OF STABILIZING AN ALKALINE AQUEOUS SOLUTION OF THIOUREA DIOXIDE

BACKGROUND OF THE INVENTION

1. Field of the Invention

This invention relates to a method of stabilizing an alkaline aqueous solution of thiourea dioxide.

2. Description of the Prior Art

Thiourea dioxide, which is also called aminoiminomethanesulfinic acid or formamidinesulfinic acid, is sold on the market industrially and is available as a white powder superior in preservative stability and having neither oxidizing property nor reducing property.

Thiourea dioxide displays reducing property when an aqueous solution thereof is made alkaline or heated, and its reducing power is very large. Besides, as compared with conventional reducing agents, e.g. sodium hydrosulfite, thiourea dioxide as powder or aqueous solution is superior in stability and scarcely produces a bad smell.

Such characteristic features of thiourea dioxide allow this substance to be used in various fields, including its application to the textile industry, for example as a reducing agent for vat dyes, a reduction clearing agent for fibers dyed with disperse dyes, a decoloring agent for fibers dyed with various dyes, a tank detergent for dyeing machines, a shrink-proofing agent for keratin fibers, a bleaching agent for protein fibers, polyamide fibers and phenolic resin fibers, a decolorizing agent to be used in the manufacturing process for polyacrylonitrile fibers and polyvinyl alcohol fibers, a white discharge printing agent for various dyes, a colored discharge printing agent, and a color fastness improver; and also its application as a pulp bleaching agent, an antioxidant for organic amines, a polymerization catalyst, a photographic sensitizing aid, an ingredient of cleaning materials, a reducing agent for metal ions, and reducing agents of organic compounds, for example as nitro compounds to hydrazo compounds or amines, ketones to secondary alcohols, aldehydes to primary alcohols, and disulfides to thiols.

Thiourea dioxide is in many cases used as an alkaline aqueous solution to display its reducing power effectively. And as alkalis there are used from strong alkalis such as caustic soda and caustic potash up to even alkali salts of weak acids such as phosphoric acid, polymerized phosphoric acid, carbonic acid, boric acid and organic acid. However, an aqueous solution of thiourea dioxide becomes easily decomposable with increasing strength of alkali. For example, a solution of thiourea dioxide dissolved in a concentrated solution of caustic soda which is one of strong alkalis decomposes gradually to a larger extent when left standing for a long time even at room temperature, and its reducing power becomes lower. Thus, in a strong alkali solution the use of thiourea dioxide often causes troubles in point of practical application, though its use in a weak alkali solution does not bring about so much decomposition thereof and so scarcely causes problem in practical application. In case thiourea dioxide and a strong alkali are dissolved together in advance and this solution is used little by little, the reducing power of the solution just after preparation differs from that after a certain elapse of time, and in the latter case it is required to use an extra amount of the solution in order to obtain the same effect.

To solve such a problem there have heretofore been adopted a method in which the solution is made concentrated beforehand in anticipation of decomposition, a method in which the solution only in a required amount is prepared just before use, and a method in which thiourea dioxide as powder is fed to a predetermined place. However, all these methods involve problems in point of economy, work and environment.

SUMMARY OF THE INVENTION

Having made various experiments and studies to prevent the decomposition of thiourea dioxide in an alkaline aqueous solution, we found that aliphatic and alicyclic ketones, as well as aliphatic dialdehydes, could afford an excellent stabilization effect and serve as an extremely advantageous stabilizer in practical application.

DESCRIPTION OF THE INVENTION

The present invention was accomplished on the basis of the above finding, and it provides an alkaline aqueous solution of thiourea dioxide which is stable over a long period of time. According to the present invention, even an aqueous thiourea dioxide solution containing a strong alkali such as caustic soda can become capable of suppressing the decomposition of thiourea dioxide by addition of one or more substances selected from aliphatic and alicyclic ketones and aliphatic dialdehydes.

To exemplify aliphatic ketones which may be used in the present invention, mention may be made of the following: acetone, methyl ethyl ketone, diethyl ketone, methyl isobutyl ketone, hydroxyacetone, propionylcarbinol, acetoin, diacetone alcohol, acetonylacetone, acetylacetone, diacetyl, and dipropionyl. Examples of alicyclic ketones are cyclohexanone, cyclopentanone, cyclohexanedione, methylcyclohexanone, and dimethylcyclohexanone.

As aliphatic dialdehydes there may be used, for example, glyoxal, malondialdehyde, succindialdehyde, glutaraldehyde, adipic dialdehyde, and maleindialdehyde.

Even if aliphatic and alicyclic ketones and aliphatic dialdehydes are used alone, they display effect, but they may also be used in combination. It is desirable that these substances are used in amounts above 0.1 mol and specially preferably from 1 to 3 moles per mol of thiourea dioxide.

DESCRIPTION OF PREFERRED EMBODIMENTS

The following examples are given to further illustrate the present invention. In these examples the concentration of thiourea dioxide was measured by the improved Knecht method, a hydrosulfite and anaylsis method, described in "Melliand Textilber, vol, 52, p. 1069 (1971)".

EXAMPLE 1

An alkaline aqueous solution of thiourea dioxide containing 10 g/l of thiourea dioxide, 30 g/l of caustic soda and a predetermined amount of a stabilizer was prepared and placed in a flask with ground stopper. The flask was dipped in a constant temperature water bath at 30° C., and the solution was sampled with the lapse of time to measure the concentration of thiourea dioxide. The decomposition rate was calculated for each stabilizer and the results of the calculation are shown in Table 1.

On the other hand, the same procedure as above was repeated with the proviso that any stabilizer was not used. The results of measurement of the decomposition rate are shown as Comparative Example in Table 1.

Table 1

| Stabilizer | | Decomposition Rate (%) | |
|---|---|---|---|
| Kind | Amount | after 2 hrs. | after 5 hrs. |
| Acetone | 1 ml/l | 13 | 30 |
| Acetone | 5 ml/l | 6 | 13 |
| Acetone | 10 ml/l | 3 | 6 |
| Acetone | 20 ml/l | 2 | 4 |
| Methyl isobutyl ketone | 10 ml/l | 4 | 10 |
| Diacetone alcohol | 20 ml/l | 2 | 6 |
| Cyclohexanone | 5 ml/l | 7 | 18 |
| Cyclohexanone | 10 ml/l | 6 | 16 |
| Glutaraldehyde | 5 g/l | 10 | 24 |
| Glutaraldehyde | 15 g/l | 5 | 13 |
| Glyoxal | 5 g/l | 7 | 25 |
| ⎡Methyl ethyl ketone | 5 ml/l | | |
| | | 5 | 12 |
| ⎣Acetoin | 5 ml/l | | |
| ⎡Methylcyclohexanone | 5 ml/l | | |
| | | 7 | 17 |
| ⎣Glutaraldehyde | 5 g/l | | |
| Comparative Example | | 16 | 38 |

EXAMPLE 2

An alkaline aqueous solution of thiourea dioxide containing 10 g/l of thiourea dioxide, 10 ml/l of acetone and caustic soda in amounts shown in Table 2 was prepared and maintained at 30° C. in a flask as in Example 1. After 5 hours, the decomposition rate was measured, the results of which are shown in Table 2.

On the other hand, the same procedure as above was repeated with the proviso that acetone was not used. The results of measurement of the decomposition rate are shown as Comparative Example in Table 2.

Table 2

| Amount of caustic soda (g/l) | Decomposition Rate (%) | |
|---|---|---|
| | Example of the present invention | Comparative Example |
| 1 | 1 | 7 |
| 5 | 2 | 13 |
| 15 | 4 | 22 |
| 30 | 6 | 38 |

We claim:

1. A method of stabilizing an alkaline aqueous solution of thiourea dioxide characterized in that one or more substances selected from the group consisting of aliphatic ketones, alicyclic ketones and aliphatic dialdehydes are added to said alkaline aqueous solution of thiourea dioxide.

2. Method according to claim 1, in which aliphatic ketone is acetone, methyl ethyl ketone, diethyl ketone, methyl isobutyl ketone, hydroxyacetone, propionylcarbinol, acetoin, diacetone alcohol, acetonylacetone, acetylacetone, diacetyl, or dipropionyl.

3. Method according to claim 1, in which alicyclic ketone is cyclohexanone, cyclopentanone, cyclohexanedione, methylcyclohexanone, or dimethylcyclohexanone.

4. Method according to claim 1, in which apliphatic dialdehyde is glyoxal, malondialdehyde, succindialdehyde, glutaraldehyde, adipic dialdehyde, or maleindialdehyde.

5. Method according to claim 1, in which said substance(s) selected from the group consisting of aliphatic ketones, alicyclic ketones and aliphatic dialdehydes is used in an amount of 0.1 to 3 mols per mol of thiourea dioxide.

* * * * *